United States Patent [19]

Sugimori et al.

[11] Patent Number: 4,699,883

[45] Date of Patent: Oct. 13, 1987

[54] PROCESS FOR PRODUCING N-ACYLNEURAMINATE ALDOLASE

[75] Inventors: Tsunetake Sugimori, Uji; Yoji Tsukada, Kyoto; Yoshihiro Uchida; Yasuhiro Ohta, both of Uji, all of Japan

[73] Assignee: Marukin Shoyu Co., Ltd., Kagawa, Japan

[21] Appl. No.: 758,116

[22] Filed: Jul. 23, 1985

[51] Int. Cl.[4] .................. C12N 9/88; C12N 15/00; C12N 1/20; C12R 1/19
[52] U.S. Cl. .................. 435/232; 435/172.1; 435/253; 435/849
[58] Field of Search .................. 435/232, 253, 172.1, 435/849

[56] References Cited

U.S. PATENT DOCUMENTS 4,492,755  1/1985  Horwath et al. .................. 435/94

FOREIGN PATENT DOCUMENTS 55-50890  4/1980  Japan .................. 435/232

OTHER PUBLICATIONS

Fermentation and Enzyme Technology, 1979, pp. 48, 49.

*Primary Examiner*—Lionel M. Shapiro
*Attorney, Agent, or Firm*—Larson and Taylor

[57] ABSTRACT

This invention provides a process for producing N-acylneuraminate aldolase comprising incubating a mutant of the genus Escherichia capable of producing N-acylneuraminate aldolase even in the absence of any inducing substance, and collecting N-acylneuraminate aldolase from the resulting culture.

2 Claims, No Drawings

PROCESS FOR PRODUCING N-ACYLNEURAMINATE ALDOLASE

This invention relates to a process for producing N-acylneuraminate aldolase.

N-Acylneuraminate aldolase, which is also called sialic acid aldolase, is a known enzyme classified with the enzyme number EC 4.1.3.3. of the Nomenclature Committee of the International Union of Biochemistry, and systematically named N-acylneuraminate: pyruvate lyase. This enzyme catalyzes the decomposition and synthesis of sialic acid (N-acylneuraminic acid) as represented by the following reaction scheme:

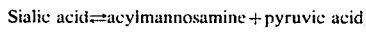

Sialic acid ⇌ acylmannosamine + pyruvic acid

We have already established a technique for producing N-acylneuraminate aldolase based on the finding that the enzyme can be easily prepared on an industrial scale by incubating known bacteria of the genus Escherichia and of several other genera in the presence of sialic acid. (Examined Japanese Patent Publication No. 54153/1981, i.e. Japanese Pat. No. 1111346). However, the established process has the disadvantage of essentially requiring addition to the culture medium of sialic acid which itself needs a cumbersome procedure for preparation and is expensive. Moreover, unless sialic acid is present, N-acylneuraminate aldolase can not be produced or is obtained only in a very small amount if possible. Thus, the process is in no way feasible industrially without using sialic acid. In other words, the microorganisms used for the above process are substantially incapable of producing N-acylneuraminate aldolase in the absence of sialic acid.

An object of the present invention is to provide a process for producing N-acylneuraminate aldolase without adding sialic acid or like inducing substance to the culture medium.

Another object of the invention is to provide microorganisms which are capable of producing a large quantity of N-acylneuraminate aldolase even in the absence of inducing substances such as sialic acid.

These objects and other features of the invention will become apparent from the following description.

The present invention provides a process for producing N-acylneuraminate aldolase comprising incubating a mutant of the genus Escherichia capable of producing N-acylneuraminate aldolase even in the absence of any inducing substance, and collecting N-acylneuraminate aldolase from the resulting culture.

The present invention further provides a biologically pure culture of a mutant of the genus Escherichia capable of producing N-acylneuraminate aldolase upon incubation in a nutrient medium containing assimilable sources of carbon, nitrogen and inorganic substance but free of any inducing substance.

We have conducted intensive research to overcome the greatest drawback of the process of the foregoing Japanese publication that it essentially requires the use of sialic acid, and to develop a process for producing a large quantity of N-acylneuraminate aldolase on an industrial scale without suing sialic acid. Consequently, we have found the face that when bacteria of the genus Escherichia, among other microorganisms used for the above process, are subjected to a mutation treatment, the resulting mutants are capable of producing a large amount of the desired enzyme even in a culture medium which is free from sialic acid or like inducing substance, i.e. the novel fact that the mutation treatment provides remarkable ability to produce N-acylneuraminate aldolase. The present invention has been accomplished based on this novel finding.

According to the present invention, the mutant produces a significant quantity of the desired enzyme in a culture medium which is usually used for the incubation of microorganisms, even if the medium is free from substances for inducing the enzyme, such as sialic acid and analogues thereof which are cumbersome to prepare. This makes it easier to produce the enzyme in large quantities on an industrial scale.

With the process of the present invention, it is critical to use mutants of the genus Escherichia. Such mutants can be prepared from known bacteria of the genus Escherichia, such as *E. coli*, *E. freundii* and *E. intermedia*, by mutating the bacterium by known means. Examples of useful means for mutation are chemical mutagenic agents such as N-methyl-N'-nitro-N-nitrosoguanidine Mitomycin C, 4-nitroquinoline-1-oxide, methyl methoanesulfonate, ethyl methanesulfonate, ethyl ethanesulfonate, 2-aminopurine, 5-bromouracil, nitrous acid, hydroxylamine, acriflavine, proflavin and acridine mustard, radiation such as x-ray irradiation, ultraviolet irradiation, etc. These means can be used singly or in a suitable combination. These means for mutation can be applied in a convention manner. For example, (a) first, a strain of the genus Escherichia is treated in an appropriate medium with the foregoing chemical mutagenic agent and/or irradiated with X ray or UV light. The concentration of the chemical mutagenic agent and time for the treatment are suitably determined according to the conventional technique used for each of the mutagenic agents. For example, N-methyl-N'-notro-N-nitrosoguanidine is used at a concentration of about 50 to about 200 µg/ml for about 0.5 to about 1 hour; ethyl methanesulfonate is used at a concentration of about 0.01 to about 0.5 M for about 0.5 to about 12 hours; 2-aminopurine is used at a concentration of about 100 to about 500 µg/ml for about 3 to about 24 hours 5-bromouracil is used at a concentration of about 20 to about 100 µg/ml for about 1 to about 12 hours; acriflavin is used at a concentration of about 1 to about 100 µg/ml for about 0.5 to about 12 hours. The concentration of other mutagenic agents and the time for the treatment is within the knowledge of the art and suitably determined. Treatment with UV light is preferably conducted by irradiating the medium for about 10 seconds to about 3 minutes with use of a mercury lamp of 10 to 15 w placed about 10 to about 70 cm above the medium. The amount of X ray to be irradiated is about 10,000 to about 100,000 Roentgen. The cells thus treated with a means for mutation are subsequently subjected to a so-called penicillin screening in a medium containing sialic acid and penicillin, thereby giving a strain which does not assimilate sialic acid. (b) Then, the sialic acid-nonassimilating strain thus obtained is isolated, and again treated with a means for mutation in the same manner as above, thereby giving revertants, i.e., strains which are capable of assimilating sialic acid. From the revertants, a strain capable of producing N-acylneuraminate aldolase in the absence of sialic acid is selected by screening.

Another method is also usable. A strain of the genus Escherichia is treated with a means for mutation in the same manner as in (a) above, and the treated cells containing the desired mutant are harvested, washed and made into a suspension having a concentration of about $10^8$ cells/ml. The suspension is inoculated in a glucose-containing medium. The inolculum is incubated, first in the glucose-containing medium for about 3 hours and then in a sialic acid-containing medium for about 3 hours, and this procedure is repeated several times, thereby concentrating the desired mutant capable of producing N-acylneuraminate aldolase in the absence of sialic acid. The cells thus obtained are incubated in a glucose-containing medium to form colonies, from which the desired mutant is selected by screening.

These mutation treatments can reproducibly give the the desired mutant capable of producing N-acylneuraminate aldolase in the absence of sialic acid.

An example of mutant which is especially suited to the present invention is *E. coli* M8328 which is obtained from *E. coli* IFO 3301 as the parent strain. The parent strain is maintained in IFO, i.e., Institute for Fermentation Osaka, 17–85, Juso-honmachi 2-chome, Yodogawa-ku, Osaka, 532, Japan and is publicly available. The strain M8328 is prepared by mutating the parent strain *E. coli* IFO 3301 in the following manner. Culture media used are adjusted to a pH of about 6 to about 7.5, preferably to 6.8 to 7.0 with use of NaOH and/or HCl. A loopful of cells of *E. coli* IFO 3301 are inoculated on a medium containing about 0.5 to about 1 wt. % of meat extract and about 0.5 to about 1 wt. % of yeast extract and preferably having a pH of 7.0 before sterilization (hereinafter referred to as "medium A") and are incubated at 30? C. with shaking. The cells are harvested in the mid-phase of logarithmic growth, washed with sterilized physiological saline and then suspended in sterilized saline to a concentration of about $1 \times 10^8$ to about $1 \times 10^9$ cells/ml, preferably about $5 \times 10^8$ cells/ml. N-Methyl-N'-nitro-N-nitrosoguanidine is added to the suspension to a final concentration of about 50 to about 200 μg/ml, preferably about 100 μg/ml, and the suspension is lightly shaken at 37° C. for about 0.5 to about 1 hour and thereafter centrifuged to collect the cells. The cells are washed with sterilized saline and then suspended in sterilized saline. A portion of the suspension is inoculated on medium A and incubated at 30? C. for about 5 to about 12 hours with shaking. The cells are collected by centriguing, washed with sterilized saline and inoculated on sodium citrate-free Davis minimal medium, i.e., a medium containing 0.2 to 0.5 wt. % of sialic acid (as the carbon source), 0.7 wt. % of dipotassium hydrogen phosphate, 0.2 wt. % of potassium dihydrogen phosphate, 0.1 wt. % of ammonium sulfate and 0.01 wt. % of magnesium sulfate (pH before sterilization preferably is 6.8, hereinafter referred to as "medium B"), followed by incubation at 37° C. for 3 hours with shaking. With addition of penicillin G to a final concentration of about 50 to about 200 U/ml, preferably about 100 U/ml, the suspension is further incubated at 37° C. for 0.5 to several hours. The cells are collected by centrifugation, washed with sterilized Physiological saline and thereafter treated by the serial-dilution technique. The desired suspension is applied to a solid medium containing 0.2 wt. % of glucose, dipotassium hydrogen phosphate, potassium dihydrogen phosphate, ammonium sulfate, magnesium sulfate and agar (pH before sterilization is preferably 6.8, the concentrations of the inorganic substances are the same as Davis minimal medium, this solid medium is hereinafter referred to as "medium C"). The inoculum is incubated at 37? C. By the replica plating technique, the resulting colonies are transferred to a solid medium prepared by adding agar to medium B (hereinafter reffered to as "medium BA") and also to medium C. The colonies are incubated at 37° C. for 12 to 24 hours, and a strain which grows on medium C but is unable to grow on medium BA is isolated as a strain which does not assimilate sialic acid. Then, in the same manner as above, the sialic acid-nonassimilating strain is incubated in medium A, and the culture is treated with N-methyl-N'-nitro-N-nitrosoguaidine and then incubated in medium A with shaking. The resulting culture is further incubated in medium C at 37° C. to form colonies, which are then applied to medium BA and medium C by the replica plating technique, followed by incubation at 37° C. for 12 to 24 hours, and a strain growing on both medium BA and medium C is isolated. The N-acylneuraminate aldolase activity of the strain is tested by the usual method for screening the strain capable of producing a large quantity of the enzyme even when incubated in a medium free from sialic acid. Thus the desired strain is obtained.

The strain M8328 thus obtained distinctly differs from the parent strain in that the former has ability to produce N-acylneuraminate aldolase in a large amount even when incubated in the absence of sialic acid. Except this feature, the strain has the same mycological characteristics as the parent strain. Accordingly, the strain is identified as a mutant of the genus Escherichia described in Part 8 of Bergey's Manual of Determinative Bacheriology (8th edition, 1974). The strain M8328 has the taxonomic characteristics disclosed in Part 8 of the Manual. The mutant was originally deposited on Feb. 13, 1984 as M8328 with the number FERM P-7446 at the Fermentation Research Institute (FRI), Agency of Industrial Science and Technology, Ministry of International Trade and Industry, 1-1-3, Higashi 1-chome, Yatabe-machi, Tsukuba-gun, Ibaraki-ken 305, Japan, and the deposit was converted to a deposit under the Budapest Treaty on Jul. 8, 1985, and assigned a number FERM BP-832.

Our research has revealed that not only the above parent strain (*E. coli* IFO 3301), but also the microorganisms useful for the process previously established by us, i.e. those of the genus Escherichia which are capable of producing N-acylneuraminate aldolase in a medium containing sialic acid, when treated with N-methyl-N'-nitro-N-nitrosoguanidine as above, can be mutated into the desired mutants having ability to produce a remarkably increased amount of the exzyme in a medium free from sialic acid. Further mutants haying comparable enzyme production ability can be derived from these microorganisms also by resorting to the various foregoing mutagenic means other than N-methyl-N'-nitro-N-nitrosoguanidine. These facts appear to indicate that the above microorganisms have latent ability to produce the enzyme, which, although usually remaining undeveloped, is expressed manifestly upon activation by the mutation treatment. At any rate, none of the microorganisms of the genus Escherichia has been known to have such remarkably improved enzyme production ability, nor is it in any way known that known microorganisms of the genus Escherichia can be made to exhibit such enzyme production ability when mutated.

The process of the present invention can be practiced by incubating the mutant of the genus Escherichia. The media to be used for incubating the microorganism are synthetic, semi-synthetic or natural media which are commonly used for incubating bacteria and which contaon assimilable nutrients such as carbon sources, nitrogen sources, inorganic compounds, etc. Examples of useful carbon sources are sugars such as glucose, fructose, invert sugar, saccharified starch, sorbitol and glycerol, organic acids such as pyruvic acid, malic acid and succinic acid, etc. Examples of useful nitrogen sources are ammonium sulfate, ammonium chloride, ammonium nitrate, ammnonium phosphate, ammonium hydroxide, ammonium tartrate, ammonium acetate, urea, etc. Examples of useful nutrients which are serviceable as both nitrogen and carbon sources are peptone, meat extract, corn steep liquor, etc. Examples of useful inorganic compounds are potassium dihydrogen phosphate, dipotassium hydrogen phosphate, sodium dihydrogen phosphate, disodium hydrogen phosphate, magnesium sulfate, magnesium chloride, potassium chloride, sodium chloride, ferrous sulfate, ferrous chloride, ferric sulfate, ferric chloride, manganese sulfate, manganese chloride, etc. Examples of other useful nutrients are yeast extract, vitamins and the like.

Although the mutant can be incubated in a liquid medium or solid medium, it is usually advantageous to use the liquid medium. For quantity production, it is especially advantageous to conduct the incubation with shaking, or with aeration and stirring. The incubation temperature is 20 to 45° C., preferably 28 to 37° C. It is desirable to adjust the medium to a pH of 6 to 9 with a suitable neurtralizing agent during incubation. When the mutant is incubated for 10 to 50 hours, the highest N-acylneuraminate aldolase acitivity is usually obtained. Since the present enzyme is generally intracellular enzyme, the enzyme is collected from the culture by harvesting the cells from the culture by centrifugation or the like, disrupting the cells by sonication, frictional rupture with glass beads or French press treatment and extracting the enzyme from the disrupted cells. The extract is treated by a conventional method, such as salting out with ammonium sulfate, ion exchange chromatography or gel filtration to obtain purified N-acylneuraminate aldolase.

The present invention will be described in greater detail with reference to the following examples, in which the N-acylneuraminate aldolase activity was measured according to the method of Barnett et al. (J. E. G. Barnett, D. L. Corina and G. Rasool, Biochemical Journal, 125, 275(1971)). One unit of enzymatic activity is defined as the amount which decomposes one micromole of N-acylneuraminic acid per minute at a reaction temperature of 37° C.

EXAMPLE 1

Into a 500-ml Erlenmeyer flask were placed 1.0 g of glucose, 0.2 g of ammonium sulfate, 0.7 g of dipotassium hydrogen phosphate, 0.2 g of potassium dihydrogen phosphate, 0.05 g of yeast extract and 100 ml of water. The mixture was adjusted to a pH of 6.8 and then sterilized by heating. The liquid medium thus prepared was inoculated with *E. coli* M8328 (FERM P-7446, FERM BP-832), and the inoculum was incubated at 30° C. with stirring for 24 hours. The cells were harvested by centrifugation, suspended in 100 ml of 25 mM phosphate buffer (pH 7.5) and disrupted by sonication. The sonicated suspension was centrifuged to separate the enzyme extract (supernatant) from the sediment. The extract was found to have an N-acylneuraminate aldolase activity of 1.02 units per ml of the extract.

For reference, the parent strain (*E. coli* IFO 3301) was similarly incubated, using the same medium as above except that the glucose was replaced by 1.0 wt. % of sialic acid (N-acylneuraminic acid). The extract obtained in the same manner as above was found to have an enzyme activity of 1.04 units per ml.

The enzyme extract (100 ml, having an enzyme activity of 102 units) thus obtained from *E. coli* M8328 was salted out by ammonium sulfate to collect a fraction of 30 to 80% saturation (as expressed by the Osborne method) on centrifugation. The precipitate was dissolved in 20 ml of 25 mM phosphate buffer (pH 7.5), followed by thorough dialysis against the same buffer. The dialyzate was lyophilized, giving 126.0 mg of a crude powder of N-acylneuraminate aldolase having an enzyme activity of 0.75 units per mg.

The crude enzyme powder can be purified into a standard product of enzyme by a usual method such as ion exchange chromatography or gel filtration.

COMPARISON EXAMPLE 1

The incubation procedure of Example 1 was repeated using the parent strain (*E. coli* IFO 3301) in place of the mutant M8328. The extract obtained was found to have an enzyme activity of 0.001 unit per ml.

COMPARISON EXAMPLE 2-4

In the same manner as in comparison Example 1, the microorganisms listed below were incubated in a medium free from sialic acid. Each extract obtained was found to have the enzyme activity listed in Table 1.

Table 1 also shownis the results achieved by incubating the organisms in a medium containing sialic acid (the same medium as used in Example 1 wherein the glucose was replaced by 1.0 wt. % of sialic acid).

TABLE 1

| | N—Acylneuraminate aldolase activity (unit) | |
|---|---|---|
| Microorganism | Sialic acid-free medium | Sialic acid-containing medium |
| *E. coli* K235 | 0.003 | 0.815 |
| *E. freundii* AKU0009 | 0.002 | 0.660 |
| *E. intermedia* AKU0010 | 0.001 | 0.631 |

EXAMPLE 2

One gram of succinic acid, 1.0 g of peptone, 1.0 g of yeast extract and 100 ml of water were placed into a 500-ml Erlenmeyer flask. The mixture was adjusted to a pH of 6.5 with sodium hydroxide and sterilized, followed by inoculating *E. coli* M8328. The inoculum was incubated at 30° C. for 20 hours. In the same manner as in Example 1, an enzyme extract was obtained, which was found to have an N-acylneuraminate aldolase activity of 1.25 units per ml.

The extract (100 ml, having an enzyme activity of 125 units) was treated by the same procedure as in Example 1 to give 143.1 mg of crude powder of N-acylneuraminate aldolase on lyophilization. The powder was found to have an enzyme activity of 0.82 unit per mg.

EXAMPLE 3

An enzyme extract was prepared in the same manner as in Example 2 except that a culture medium containing 1 wt. % of a carbon source as listed in Table 2, 1 wt. % of yeast extract and 1 wt. % of peptone and adjusted to a pH of 6.8 to 7.0 was used.

Table 2 below shows the enzyme activity of the resulting extract.

TABLE 2

| Carbon source | N—acylneuraminate aldolase activity (U/ml) |
| --- | --- |
| Galactose | 1.15 |
| Lactose | 1.00 |
| Xylose | 0.95 |
| Glycerol | 0.90 |
| Sorbitol | 1.00 |
| Malic acid | 1.15 |
| Pyruvic acid | 1.00 |
| N—acetylgalactosamine | 1.10 |
| Ethanol | 0.97 |

We claim:

1. A process for producing N-acylneuraminate aldolase comprising incubating a mutant of the genus Escherichica having all the identifying characteristics of FERM BP-832 and capable of producing N-acylneuraminate aldolase even in the absence of any inducing substance, and collecting N-acylneuraminate aldolase from the resulting culture.

2. A biologically pure culture of a mutant of the genus Escherichia capable of producing N-acylneuraminate aldolase upon incubation in a nutrient medium containing assimilable sources of carbon, nitrogen and inorganic substance but free of any inducing substance, wherein the mutant has all the identifying characteristics of FERM BP-832.

* * * * *